United States Patent
Blanda et al.

(10) Patent No.: US 7,399,348 B2
(45) Date of Patent: Jul. 15, 2008

(54) LOW SURFACE TENSION SURFACTANTS BASED ON AMINO ALCOHOL AND THEIR USE

(75) Inventors: Gaetano Blanda, Segrate-Milano (IT); Ingrid Eiβmann, Gelsenkirchen (DE); Kathrin Lehmann, Leverkusen (DE); Heike Lüther, Mülheim an der Ruhr (DE); Stefan Silber, Krefeld (DE); Philipp Tomuschat, Essen (DE)

(73) Assignee: Goldschmidt GmbH, Essen (DE)

( * ) Notice: Subject to any disclaimer, the term of this patent is extended or adjusted under 35 U.S.C. 154(b) by 396 days.

(21) Appl. No.: 10/844,818

(22) Filed: May 12, 2004

(65) Prior Publication Data

US 2004/0229768 A1 Nov. 18, 2004

(30) Foreign Application Priority Data

May 14, 2003 (DE) ............................. 103 21 536

(51) Int. Cl.
 *C09D 1/00* (2006.01)
 *C11D 7/26* (2006.01)
 *C11D 7/32* (2006.01)
(52) U.S. Cl. .................. 106/3; 106/14.15; 510/499; 510/505; 510/506
(58) Field of Classification Search ................ None
 See application file for complete search history.

(56) References Cited

U.S. PATENT DOCUMENTS

| | | | |
|---|---|---|---|
| 2,819,222 A | 1/1958 | De Groote | |
| 2,997,447 A | 8/1961 | Russell | |
| 3,515,698 A | 6/1970 | Mauz | |
| 3,697,458 A | 10/1972 | Burba | |
| 3,853,770 A | 12/1974 | Altschuler | |
| 4,151,204 A * | 4/1979 | Ichikawa et al. ............ | 564/480 |
| 4,163,815 A | 8/1979 | Cheung | |
| 4,406,826 A | 9/1983 | Morgan | |
| 4,940,770 A * | 7/1990 | Speranza et al. ............ | 528/111 |
| 5,681,907 A * | 10/1997 | Starner et al. ................ | 525/526 |
| 6,140,541 A * | 10/2000 | Melder et al. ................ | 564/475 |
| 2004/0082794 A1* | 4/2004 | Yokozawa et al. .......... | 546/304 |
| 2006/0183830 A1* | 8/2006 | Friedrich et al. ............ | 524/236 |

FOREIGN PATENT DOCUMENTS

| | | |
|---|---|---|
| EP | 0017189 A | 10/1980 |
| EP | 0114722 A | 8/1984 |
| EP | 0897744 B1 | 2/2001 |
| EP | 1277829 A | 1/2003 |
| GB | 1320453 A | 6/1973 |
| JP | 60001239 A2 | 1/1985 |
| JP | 60231723 A2 | 11/1985 |
| JP | 02080600 A2 | 3/1990 |
| JP | 06166994 A2 | 6/1994 |
| JP | 07159915 A2 | 6/1995 |
| JP | 2001059009 A2 | 3/2001 |
| JP | 2001207380 A2 | 8/2001 |
| WO | WO-9718889 A | 5/1997 |
| WO | WO-0248249 A | 6/2002 |

OTHER PUBLICATIONS

Journal of Surfactants and Detergents (1999), 2(3), 349-355. Abstract.*
Okano, T., The crosslinking reaction of telechelic diamino dihydroxy oligormers with cyanuric chloride by the method, Nippon Kagaku Kaishi, (1977) (11), 1707-10.
Zarkhina, T.S., Mechanism of thermal degradation of low-molecular-weight compounds modeling, Vysokomolekulyarnye Soedineniya, Seriya A, (1982), 24 (3), 584-95.
Terent'ev, A.P., Aminopropanediol derivatives. II., Zuhumal Obshchei Khimii (1962), 32, 174-7.
Takezawa, T., Hydrolase models of bis-quaternary ammonium salts, Nihon Yukagakkaishi (1999), 48 (3), 227-233.
Bassilana, C., Synthesis of new b-hydroxylated and b-carboxylated bisquarternary ammonium salts containing fluorinated, Journal of Fluorine Chemistry 92 (1998) 109-117.

* cited by examiner

*Primary Examiner*—Gregory R Del Cotto
(74) *Attorney, Agent, or Firm*—Frommer Lawrence & Haug LLP

(57) ABSTRACT

The invention provides low surface tension surfactants based on amino alcohol and also provides for their use in aqueous coating formulations, said surfactants being preparable by reacting at least one secondary amine of formula (I):

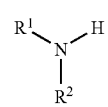

(I)

with at least one diepoxide of formula (IV):

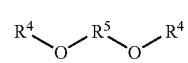

(III)

and/or with at least one triepoxide of formula (IV):

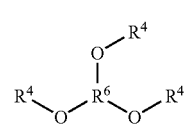

(IV)

in essentially equivalent amounts of amine hydrogen atoms and epoxide groups.

7 Claims, No Drawings

LOW SURFACE TENSION SURFACTANTS BASED ON AMINO ALCOHOL AND THEIR USE

RELATED APPLICATIONS

This application claims priority to German application Ser. No. 103 21 536.0, filed on May 14, 2003, incorporated herein by reference.

FEILD OF THE INVENTION

The invention relates to low surface tension surfactants based on amino alcohol and to their use in aqueous coating formulations.

BACKGROUND OF THE INVENTION

Water-based paints and coatings are used on a large scale industrially. Critical to effective wetting of the substrate is the lowering of the surface tension of the aqueous system by means of a surfactant. It is not only the lowering of the static surface tension to a small value that is decisive here, but also the corresponding lowering of the dynamic surface tension. A low dynamic surface tension is needed in particular for high-speed applications: for example, when applying coatings by spraying, or in printing operations. Furthermore, the surfactants used must not create any surface defects, must not cause any turbidity, and should be low-foaming. That means, they should not promote the build-up of significant amounts of foam.

Although nonionic surfactants such as alkylaryl ethoxylates or alcohol ethoxylates or ethylene oxide (EO)-propylene oxide (PO) copolymers are for sure capable of reducing the static surface tension, the high molecular weight and resultant low molecular mobility of these classes of compounds mean that it is not possible to lower the dynamic surface tension to a value which is acceptable to the user.

Conversely, some anionic surfactants, such as the sodium salts of monoalkyl or dialkyl sulfosuccinates, are able effectively to reduce the dynamic surface tension, but using them leads to severe build-up of foam in application, and the finished coating reacts sensitively to water.

More recently a new class of surfactants has been developed based on acetylenic glycols and their alkoxylates. The properties of these surfactants are situated between those of the surfactants outlined above. With these new surfactants it is possible to reduce both the static and the dynamic surface tension, with the values which can be achieved not entirely matching those of the nonionic and anionic surfactants. But, on the plus side, these surfactants provide comparatively low-foam formulations (EP-B-0 897 744, U.S. Pat. No. 2,997, 447).

In view of these properties, surfactants of this kind have been able to establish themselves convincingly in numerous applications. Their properties are primarily attributed to the rigid acetylenic alkyl spacer, which, as a result of the restricted degrees of freedom, dictates a kind of preorientation of polar and nonpolar groups. Responsibility for these properties is additionally ascribed to the small distance between the polar groups and to the low molecular weight (<300 g/mol), which allows the surfactant molecules to be highly mobile.

A problem with compounds of this type is that, in applications, foam build-up reoccurs after a very short time. For the user, on the other hand, it is very important to prevent this new foam build-up for as long as possible. The alternative would be to add defoamers, whose possible consequences include unwanted defects of the coating film and problems with interlayer adhesion.

There was therefore a need to provide compounds which not only allow effective reduction in static and dynamic surface tension but also prevent foam build-up/new foam build-up effectively for a long period of time; i.e., e.g., a time period greater than 60 seconds.

In an effort to overcome the disadvantages of the prior art and to provide compounds which significantly reduce dynamic surface tension and at the same time effectively inhibit the (re)formation of foam for a long time it has now surprisingly been found that this objective can be achieved by means of amino alcohols preparable by reacting amines, preferably secondary amines, containing at least one amine hydrogen with glycidyl compounds.

SUMMARY OF THE INVENTION

The invention accordingly provides amino alcohols obtained by reacting one or more amines of formula (I)

in which $R^1$ and $R^2$ independently from each other are each a branched or unbranched, saturated or unsaturated residue with or without a hydroxyl group or other heteroatom substituents and containing 1 to 30 carbon atoms, or a group of the general formula (II)

$$R^3—X—(CH_2)_a—\quad\quad(II)$$

in which $R^3$ is a branched or unbranched, saturated or unsaturated residue with or without a hydroxyl group or other heteroatom substituents and containing 1 to 30 carbon atoms, X is a residue from the group —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, and —N(CH$_3$)—S(O$_2$)—, and a is an integral variable between 1 and 4, with an epoxide of formula (III)

where $R^4$ independently at each occurrence is H or 2,3-epoxypropyl, with the proviso that on average there is more than one, preferably more than one and a half, 2,3-epoxypropyl residue (s) in the molecule, and $R^5$ is a branched or unbranched, saturated or unsaturated residue with or without a hydroxyl group or other heteroatom substituents and containing 1 to 30 carbon atoms;

and/or by reacting one or more amines of formula (I) above with an epoxide of formula (IV)

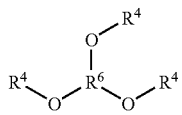

(IV)

where
R⁴ independently at each occurrence is H or 2,3-epoxypropyl, with the proviso that there are on average at least about two 2,3-epoxypropyl residues in the molecule, and
R⁶ is a branched or unbranched, saturated or unsaturated residue with or without a hydroxyl group or other heteroatom substituents and containing 1 to 30 carbon atoms.

The invention further provides amino alcohols of the general formulae (V) and (VI)

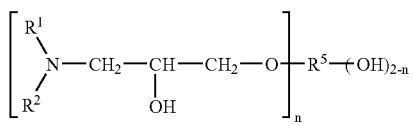

(V)

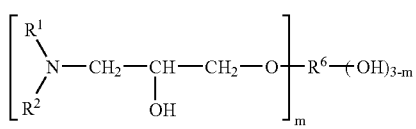

(VI)

preparable by the above reaction, in which
$R^1$ and $R^2$ are as defined above and independently from each other are preferably branched or unbranched alkylene residues having 1 to 10, in particular 3 to 6, carbon atoms, and/or $R^3$—X—$(CH_2)_a$— where $R^3$, X, and a are as defined above, $R^3$ preferably being a branched or unbranched alkyl residue having 1 to 10, in particular 2 to 8, carbon atoms, X preferably being —(O)C—NH—, and a preferably being 3,
$R^5$ and $R^6$ are as defined above, and independently from each other are preferably branched or unbranched alkylene residues having 1 to 10, in particular 3 to 6, carbon atoms, and
n is 1 to 2, preferably >1.5 to 2, and in particular about 2, and
m is 1 to 3, preferably >1.5 to 2.5, and in particular about 2.

The invention additionally provides for the use of the amino alcohols of the invention as additives which reduce surface tension and at the same time inhibit the (re)formation of foam effectively for a long time in aqueous formulations, especially aqueous formulations for surface coatings, paints, printing inks or varnishes.

The invention further provides aqueous formulations comprising at least one of the amino alcohols of the invention in amounts from about 0.05% to about 5%, preferably from about 0.1% to about 3%.

DETAILED DESCRIPTION OF THE INVENTION

The amines and glycidyl ethers used in accordance with the invention are industrial products which can be employed in the form of their respective commercially customary specifications, although in specialty applications of the amino alcohols of the invention higher levels of purity may be required.

Particularly preferred residues $R^1$ and $R^2$ in the amine are n-propyl, isopropyl, n-butyl, and isobutyl residues, or the amido aminies preparable from short-chain carboxylic acids with amines of the formula X—$(CH_2)_a$—NH—$R^1$ or X—$(CH_2)_a$—NH—$R^2$ where X is $NH_2$ and a is 2 or 3.

Diglycidyl ethers used are preferably ethylene glycol diglycidyl ether, 1,2-propanediol diglycidyl ether, 1,3-butanediol diglycidyl ether, 1,4-butanediol diglycidyl ether, neopentyl glycol diglycidyl ether, cyclohexane dimethanol diglycidyl ether, diethylene glycol diglycidyl ether, dipropylene glycol diglycidyl ether, polyethylene glycol diglycidyl ethers, polypropylene glycol diglycidyl ethers, glycerol diglycidyl ether, resorcinol diglycidyl ether, 2,2-bis(4-glycidyloxyphenyl)propane, bis(4-glycidyloxyphenyl)-methane, bisphenol A propoxylate (1-PO/phenol) diglycidyl ether, and diglycidyl 1,2-cyclohexanedicarboxylate.

As triglycidyl ethers it is preferred to use glycerol triglycidyl ether, trimethylolpropane triglycidyl ether, and triphenylolmethane triglycidyl ether.

Particularly preferred glycidyl compounds are those having two or three functional groups, such as butanediol diglycidyl ether, neopentyl glycol diglycidyl ether, trimethylolpropane triglycidyl ether, and glycerol diglycidyl ether.

Amines and glycidyl compounds are preferably used in approximately equivalent amounts based on reactive amine hydrogen atoms and epoxide groups. The basis for calculation are the amine number and epoxide values which are familiar to the skilled worker.

Experimental Section:
The following non-limiting examples serve to illustrate the invention.
Complete conversion in all reactions was verified by $^1$H NMR measurements.

EXAMPLE 1

Reaction of Butanediol Diglycidyl Ether with Hexanamidopropylmonomethylamine 50 g of 81% hexanamidopropylmonomethylamine (0.22 mol) were heated to 50° C. with stirring under nitrogen. Then 23.1 g (0.11 mol) of butanediol diglycidyl ether were slowly added dropwise. When addition was complete the mixture was stirred at 70° C. for 5 h. When reaction was at an end the product was cooled to give an orange-colored liquid of high viscosity.

EXAMPLE 2

Reaction of Butanediol Diglycidyl Ether with Diisopropylamine 50 g (0.5 mol) of diisopropylamine were heated to 50° C. with stirring under nitrogen. Then 49.9 g (0.25 mol) of butanediol diglycidyl ether were slowly added dropwise. When addition was complete the mixture was stirred at 70° C. for 5 h. When reaction was at an end the product was cooled to give a pale yellow liquid.

EXAMPLE 3

Reaction of Butanediol Diglycidyl Ether with di-n-Butylamine 50 g (0.39 mol) di-n-butylamine were heated to 50° C. with stirring under nitrogen. Then 39.1 g (0.19 mol) of butanediol diglycidyl ether were slowly added dropwise. When addition was complete the mixture was stirred at 70° C. for 5 h. When reaction was at an end the product was cooled to give a yellow liquid.

EXAMPLE 4

Reaction of Butanediol Diglycidyl Ether with Diisobutylamine

A mixture of 25.6 g (0.20 mol) of diisobutylamine and 20.0 g (0.10 mol) of butanediol diglycidyl ether was heated at 120° C. for 10 h with stirring under nitrogen. When reaction was at an end the product was cooled to give a yellow liquid.

EXAMPLE 5

Reaction of Butanediol Diglycidyl Ether with di-n-pentylamine 50 g (0.32 mol) di-n-pentylamine were heated to 50° C. with stirring under nitrogen. Then 32.1 g (0.16 mol) of butanediol diglycidyl ether were slowly added dropwise. When addition was complete the mixture was stirred at 70° C. for 8 h. When reaction was at an end the product was cooled to give a yellow liquid.

EXAMPLE 6

Reaction of Neopentyl Glycol Diglycidyl Ether with di-n-butylamine

A mixture of 20.5 g (0.16 mol) of di-n-butylamine and 20.0 g 86% of neopentyl glycol diglycidyl ether (0.08 mol) was heated at 110° C. for 14 h with stirring under nitrogen. When reaction was at an end the product was cooled to give a yellow liquid.

EXAMPLE 7

Reaction of Neopentyl Glycol Diglycidyl Ether with Diisobutylamine

A mixture of 20.5 g (0.16 mol) of diisobutylamine and 20.0 g 86% of neopentyl glycol diglycidyl ether (0.08 mol) was heated at 120° C. for 14 h with stirring under nitrogen. When reaction was at an end the product was cooled to give a yellow liquid.

EXAMPLE 8

Reaction of Glycerol Diglycidyl Ether with di-n-butylamine

A mixture of 18.4 g (0.14 mol) of di-n-butylamine and 20.0 g 73% of glycerol diglycidyl ether (0.07 mol) was heated at 100° C. for 14 h with stirring under nitrogen. When reaction was at an end the product was cooled to give a pale yellow liquid.

EXAMPLE 9

Reaction of Glycerol Diglycidyl Ether with Diisobutylamine

A mixture of 18.4 g (0.14 mol) of diisobutylamine and 20.0 g 73% of glycerol diglycidyl ether (0.07 mol) was heated at 100° C. for 12 h with stirring under nitrogen. When reaction was at an end the product was cooled to give a pale yellow liquid.

EXAMPLE 10

Reaction of Polypropylene Glycol Diglycidyl Ether with di-n-butylamine

A mixture of 14.1 g (0.11 mol) of di-n-butylamine and 20.0 g of polypropylene glycol diglycidyl ether (0.055 mol) was heated at 100° C. for 14 h with stirring under nitrogen. When reaction was at an end the product was cooled to give a viscous yellow liquid.

EXAMPLE 11

Reaction of Polypropylene Glycol Diglycidyl Ether with Diisobutylamine

A mixture of 14.1 g (0.11 mol) of diisobutylamine and 20.0 g of polypropylene glycol diglycidyl ether (0.055 mol) was heated at 100° C. for 14 h with stirring under nitrogen. When reaction was at an end the product was cooled to give a viscous orange-colored liquid.

EXAMPLE 12

Reaction of Trimethylolpropane Triglycidyl Ether with di-n-butylamine

A mixture of 18 g (0.14 mol) of di-n-butylamine and 20.0 g 70% of trimethylolpropane triglycidyl ether (0.05 mol) was heated at 100° C. for 14 h with stirring under nitrogen. When reaction was at an end the product was cooled to give a viscous yellow liquid.

EXAMPLE 13

Reaction of Trimethylolpropane Triglycidyl Ether with Diisobutylamine

A mixture of 18 g (0.14 mol) of diisobutylamine and 20.0 g 70% of trimethylolpropane triglycidyl ether (0.05 mol) was heated at 120° C. for 14 h with stirring under nitrogen. When reaction was at an end the product was cooled to give a viscous yellow liquid.

Application Tests:

For the testing of new wetting agents a skilled worker performs a series of overview tests in order to assess not only the inhibitory and/or preventative effect on foam but also the rapid, surfactant-initiated destruction of foam formed in a system by other surface-active substances. Another important criterion for grading surfactants is their long-term effect in the sense of preventing foam even after storage of the corresponding system equipped with the wetting agent.

Dynamic Surface Tension:

Determining the dynamic surface tension of the formulated systems is essential to be able to estimate the rate at which a wetting agent molecule reaches a newly generated interface in order to be able to make an active contribution to destroying foam.

These values are determined using the online tensiometer t 60 from SITA Messtechnik GmbH. This instrument measures the dynamic surface tension in accordance with the principle of maximum bubble pressure: the internal force of attraction of a liquid also compresses those air bubbles present in the liquid. The resultant pressure increases as the bubble radius falls. It is this pressure, increased in relation to the ambient pressure, that is utilized for the bubble pressure method. A gas stream is passed through a capillary, which is dipped in a liquid. The bubble surface which forms becomes curved and continuously reduces the radius of the bubble. The pressure increases up to a maximum value. At this value the bubble has attained its smallest radius, the capillary radius, and forms a hemisphere. When this point is exceeded the bubble bursts and tears away from the capillary, allowing a new bubble to form. This produces a characteristic pressure curve, which is evaluated in order to determine the surface tension. In other words, the smaller the value in the case of low bubble frequency, the more effective the wetting agent in wetting a low-energy surface. The smaller the difference between the value at low bubble frequency and the value at high bubble frequency, the more capable the wetting agent of orienting itself to newly created surfaces—that is, in being effective even during highly dynamic application processes.

The wetting agents claimed in accordance with the invention were evaluated by carrying out the tests set out in greater detail below.

Foam Inhibition Effect:

A defined amount of wetting agent is added to a defined amount of a test system and is incorporated using a toothed-wheel disk at 1 500 rpm for 1 minute. Subsequently air is introduced at 3 000 rpm for 1 minute, and foam produced. The resulting foam height is read off and viewed in comparison with the foam height reached in the absence of the wetting agent. Thereafter a measurement is made of the time taken for the foam to go down completely, something which generally does not happen at all in the absence of wetting agents.

Assessment of Foam Build-Up and of Spontaneous Defoaming:

Foam is built up in a defined amount of a test system using a perforated disk (see below) at 2 000 rpm for 1 minute. Then a defined amount of wetting agent is placed on the foam and the occurrence of spontaneous defoaming is assessed visually (bursting air bubbles, "prickling" on the surface) and graded as absent (−), present (+/−) or very characteristic (+).

Shearing with the perforated disk is then repeated at 2 000 rpm for one minute. This time a stopwatch is used to record the time which elapses before foam builds up again. If a wetting agent is able to prevent foam building up again, it is classified, with ">60 s" as very active.

If the wetting agent further reduces the foam during shearing, the classification "no further foam build-up" in conjunction with very low foam heights characterizes the wetting agent as a low-foam agent.

A defined amount of this sample is subsequently introduced into a measuring cylinder and the foam height is recorded by reporting ml of foam and is compared with a blank sample.

The perforated disk employed actually comprises three disks arranged one above the other on a spindle (disk thickness 3 mm, disk diameter 25 mm) and each having three holes (diameter: 5 mm). The distance between the individual disks is 9 mm and they rotate vertically by 120° on the spindle. This apparatus allows optimum introduction of macrofoam and microfoam, such as occurs in painting application operations (such as rolling or spraying, for example) and production processes and can be prevented by suitable wetting agents.

Long-Term Effect:

Following storage of the twice-sheared sample (see test described above) for 4 to 14 days the sample is again stirred with the perforated disk at 2 000 rpm for 1 minute and again the resulting foam height of the sample is read off in a measuring cylinder. Where there is hardly any difference between these values and the original determination, the wetting agent is still available in the system and hence is also found to be stable to hydrolysis.

In the following tests the wetting agents of the invention are labeled S1, S2, and S3.

S1 butanediol diglycidyl ether with diisobutylamine (example 4)

S2 neopentyl diglycidyl ether with diisobutylamine (example 7)

S3 glycerol diglycidyl ether with diisobutylamine (example 9)

Noninventive, comparative examples are the following wetting agents, which are supplied as commercial products for aqueous systems and can be characterized in accordance with the details below.

C1 2,4,7,9-tetramethyl-5-decyne-4,7-diol in ethylene glycol (50% strength solution)

C2 2,4,7,9-tetramethyl-5-decyne-4,7-diol ethoxylate

C3 fatty alcohol alkoxylate with a molar weight of about 500 g/mol

The aforementioned inventive and commercially customary wetting agents were deployed in the standard formulations below.

Water-Based Printing Ink Formulation:

50 g of ink, consisting of:

JonCryl® 8085 (43% ammoniacal solution of an acrylate resin)[1] 29.4 g

JonCryl® ECO 2189 (glycol-ether-free, film-forming polymer dispersion)[1] 44.1 g JonCryl® ECO, 2177 (glycol-ether-free, film-forming polymer dispersion)[1] 17.7 g JonWax® 35 (polyethylene wax emulsion)[1] 4.9 g demineralized water 2.9 g

[1] Johnson Polymer were weighed out into a 100 ml glass bottle, 0.5% of active matter of wetting agent was stirred in using a 2.5 cm toothed-edge disk at 1 500 rpm for 1 minute, and the mixture was then foamed at 3 000 rpm for 1 minute. The fill level (solution+foam) was read off in the glass bottle using a ruler and the time taken for the foam to collapse, in minutes, was determined using a stopwatch. For determining the dynamic surface tension, 12 g of water were added to 48 g of ink containing 0.5% wetting agent. The mixture was homogenized by simple shaking.

TABLE 1

Results in a water-based printing ink:

| Wetting agent | Foam [cm] | Time to foam collapse [min] | Dynamic surface tension with 2 and 10 bubbles/sec [mN/m] |
|---|---|---|---|
| non | 7.0 | stable, >12 h | 43.0-55.7 |
| S1 | 4.7 | 180* | 40.4-53.9 |
| S2 | 5.5 | 120* | 41.4-52.8 |
| S3 | 5.5 | 60* | 40.4-49.4 |
| C1 | 6.0 | stable, >12 h | 39.6-51.8 |
| C2 | 5.5 | stable, >12 h | 42.7-55.1 |
| C3 | 6.7 | stable, >12 h | 42.7-55.0 |

*Residual amount of less than 1% of the original amount of foam reached

Table 1 shows that using the wetting agents claimed in accordance with the invention reduces foam build-up as compared with the blank sample and with the comparative examples. As a result, the class of substance claimed in accordance with the invention is able to ensure complete defoaming.

Water-Based Automotive Finish:

50 g of a mixture of 2 parts of aliphatic polyurethane-acrylic hybrid dispersion Daotan® VTW 6264 (Solutia) and 1 part of DI (deionized) water in a vessel (diameter: 65 mm) were foamed at 2 000 rpm for 1 minute using a perforated disk (for description see above). 0.2% of active matter of wetting agent ingredient was placed on the resulting foam, and the spontaneous defoaming was observed. This was followed by shearing again at 2 000 rpm for 1 minute, after which the time taken for the foam to build up again was measured using a stopwatch. If the foam does not build up again, the evaluation is reported as >60 seconds.

Immediately following the shearing operation, 25 g of this sample are introduced into a 100 ml measuring cylinder, and the fill level was read off in ml.

In order to assess the stability to hydrolysis and the storage stability the sample after four days was again sheared at 2 000 rpm for 1 minute and the foam height of 25 g was determined using a 100 ml measuring cylinder.

TABLE 2

Results in an aqueous automotive finish:

| Wetting agent | Spontaneous defoaming* | Renewed build-up of foam [sec] | Foam value instantaneous [ml/25 g] | Foam value after 4 days [ml/25 g] |
|---|---|---|---|---|
| blank value | n/a | n/a | 44 | 46 |
| S1 | +/− | >60 | 27 | 29 |
| S2 | +/− | >60 | 28 | 30 |
| S3 | +/− | >60 | 29 | 31 |
| C1 | + | 45 | 30 | 32 |
| C2 | +/− | >60 | 37 | 40 |
| C3 | + | 45 | 30 | 33 |

*(−) absent,
(+/−) present,
(+) very marked

The compounds of the invention exhibit effective spontaneous defoaming, further introduction of shearing being accompanied by a significant defoaming which the comparative substances are unable to perform. This enormous potential of the compounds of the invention is also present after the systems have been stored, so that it is necessary neither to add further wetting agent nor to use additional defoamer.

SUMMARY

The wetting agents group claimed in accordance with the invention can not only be used as a spontaneous defoamer, but providing samples with such wetting agents at the start when preparing the systems provides foam inhibition even following storage and on later use of the systems.

The above description is intended to be illustrative and not limiting. Various changes in the embodiments described herein may occur to those skilled in the art. These changes can be made without departing from the scope or spirit of the invention.

What is claimed is:

1. An amino alcohol of the formula (V) or (VI)

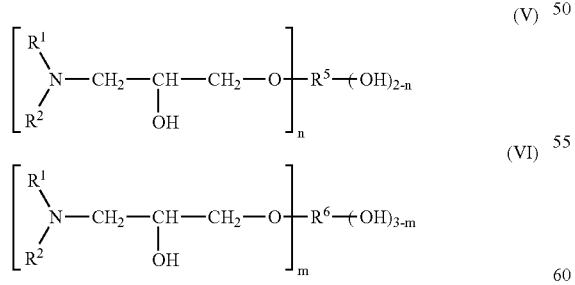

in which
R$^1$ and R$^2$ independently of each other are each a branched or unbranched, saturated or unsaturated C$_1$-C$_{30}$ hydrocarbyl radical, or a group of the formula (II):

$$R^3\text{---}X\text{---}(CH_2)_a\text{---} \qquad (II)$$

in which
R$^3$ is a branched or unbranched, saturated or unsaturated hydrocarbon C$_1$-C$_{30}$ group optionally substituted by at least one hydroxyl group and wherein at least one of the carbon atoms is optionally replaced be a heteroatom,
X is a residue selected from the group consisting of —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, and —N(CH$_3$)—S(O$_2$)—, and
a is an integer between 1 and 4,
m is 1 to 3,
n is 1 to 2,
R$^5$ is a branched or unbranched, saturated or unsaturated residue with or without a hydroxyl group or other heteroatom substituents and containing 1 to 30 carbon atoms; and
R$^6$ is a branched or unbranched, saturated or unsaturated residue with or without a hydroxyl group or other heteroatom substituents and containing 1 to 30 carbon atoms.

2. The amino alcohol as claimed in claim 1 wherein
R$^1$ and R$^2$ independently of each other are each a branched or unbranched, saturated or unsaturated C$_1$-C$_{10}$ hydrocarbyl radical, or a group of the formula (II):

$$R^3\text{---}X\text{---}(CH_2)_a\text{---} \qquad (II)$$

in which
R$^3$ is a branched or unbranched, saturated or unsaturated hydrocarbon C$_1$-C$_{10}$ group optionally substituted by at least one hydroxyl group,
X is a residue selected from the group consisting of —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, and —N(CH$_3$)—S(O$_2$)—, and
a is an integer between 1 and 4,
m is >1.5 to 2.54,
n is >1.5 to 2.

3. The amino alcohol as claimed in claim 1 wherein
R$^1$ and R$^2$ are independently of one another a branched or unbranched alkylene group having 3 to 6 carbon atoms, anchor R$^3$—X—(CH$_2$)$_a$—where R$^3$ is a branched or unbranched alkyl group having 2 to 8 carbon atoms, X is —(O)C—NH—, and a is 3, and R$^5$ and R$^6$ are independently of one another branched or unbranched alkylene groups having 3 to 6 carbon atoms, and
n is 2, and
m is 2.

4. A method for reducing the surface tension in an aqueous formulation while at the same time inhibiting the re-formation of a foam for a long period of time which comprises adding an effective amount of at least one amino alcohol according to claim 1 in amounts from about 0.05% to about 5%.

5. An aqueous formulation which comprises at least one amino alcohol as claimed in claim 1 and water.

6. The aqueous formulation as claimed in claim 5, which is a surface coating, paint, printing ink or varnish.

7. A car polish which comprises the aqueous formulation according to claim 5.

* * * * *